US00PP19752P2

(12) United States Plant Patent
Dekker

(10) Patent No.: US PP19,752 P2
(45) Date of Patent: Feb. 17, 2009

(54) ***CHRYSANTHEMUM* PLANT NAMED 'DEKNAVONA'**

(50) Latin Name: *Chrysanthemum×morifolium*
Varietal Denomination: Deknavona

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/151,161

(22) Filed: May 2, 2008

(51) Int. Cl.
*A01H 5/00* (2006.01)

(52) U.S. Cl. ..... Plt./287

(58) Field of Classification Search ..... Plt./287
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Chrysanthemum* plant named 'Deknavona', characterized by its decorative-type inflorescences with pale pink and purple-colored ray florets; strong and upright flowering stems; freely flowering habit; early and uniform flowering response; and good postproduction longevity.

2 Drawing Sheets

Botanical designation: *Chrysanthemum×morifolium.*
Cultivar denomination: 'Deknavona'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Deknavona'.

The new *Chrysanthemum* is a product of a planned breeding program conducted by the Inventor in Hensbroek, The Netherlands. The objective of the breeding program is to create new freely flowering decorative-type *Chrysanthemum* cultivars with unique ray floret coloration and excellent postproduction longevity.

The new *Chrysanthemum* originated from a cross-pollination made by the Inventor in Hensbroek, The Netherlands on Jan. 20, 2005 of a proprietary selection of *Chrysanthemum×morifolium* identified as code number 00.4758.04, not patented, as the female, or seed, parent with a proprietary selection of *Chrysanthemum×morifolium* identified as code number 41241, not patented. The new *Chrysanthemum* was discovered and selected by the Inventor as a flowering plant from within the progeny of the stated cross-pollination in a controlled greenhouse environment in Hensbroek, The Netherlands on Oct. 12, 2005.

Asexual reproduction of the new *Chrysanthemum* by terminal cuttings in a controlled greenhouse environment in Hensbroek, The Netherlands since Oct. 28, 2005, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deknavona'. These characteristics in combination distinguish 'Deknavona' as a new and distinct cultivar of *Chrysanthemum:*

1. Decorative-type inflorescences with purple and pale pink-colored ray florets.
2. Strong and upright flowering stems.
3. Freely flowering habit.
4. Early and uniform flowering response; plants flower about seven weeks after the start of photoinductive treatments.
5. Good postproduction longevity; plants maintain good substance for about four weeks in an interior environment.

Plants of the new *Chrysanthemum* differ from plants of the female parent selection in the following characteristics:

1. Plants of the new *Chrysanthemum* are not as vigorous as plants of the female parent selection.
2. Plants of the new *Chrysanthemum* have larger inflorescences than plants of the female parent selection.
3. Plants of the new *Chrysanthemum* flower earlier than plants of the female parent selection.
4. Plants of the new *Chrysanthemum* and the female parent selection differ in ray floret color as plants of the female parent selection have pink-colored ray florets.

Plants of the new *Chrysanthemum* differ from plants of the male parent selection in the following characteristics:

1. Plants of the new *Chrysanthemum* have smaller leaves than plants of the male parent selection.
2. Plants of the new *Chrysanthemum* have smaller inflorescences than plants of the male parent selection.
3. Plants of the new *Chrysanthemum* flower earlier than plants of the male parent selection.

Plants of the new *Chrysanthemum* can be compared to plants of the *Chrysanthemum×morifolium* 'Lollipop', not patented. In side-by-side comparisons conducted in Hensbroek, The Netherlands, plants of the new *Chrysanthemum* differed from plants of 'Lollipop' in the following characteristics:

1. Plants of the new *Chrysanthemum* were not as vigorous as plants of 'Lollipop'.
2. Plants of the new *Chrysanthemum* had smaller leaves than plants of 'Lollipop'.
3. Plants of the new *Chrysanthemum* had smaller inflorescences than plants of 'Lollipop'.
4. Plants of the new *Chrysanthemum* flowered earlier than plants of 'Lollipop'.

BRIEF DESCRIPTION OF THE PHOTOGRAPHS

The accompanying colored photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering stem of 'Deknavona' grown as a spray type.

The photograph on the second sheet is a close-up of a typical flowering stem of 'Deknavona'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter and early spring in Hensbroek, The Netherlands, under commercial practice in a glass-covered greenhouse. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were about nine weeks from planting when the photographs and the description were taken.

Botanical classification: *Chrysanthemum×morifolium* 'Deknavona'.

Parentage:

*Female, or seed, parent.*—Proprietary selection of *Chrysanthemum×morifolium* identified as code number 00.4758.04, not patented.

*Male, or pollen, parent.*—Proprietary selection of *Chrysanthemum×morifolium* identified as code number 41241, not patented.

Propagation:

*Type.*—Terminal vegetative cuttings.

*Time to initiate roots.*—About four to six days at 20° C.

*Time to produce a rooted young plant.*—About 13 to 15 days at 20° C.

*Root description.*—Fine, fibrous; light brown in color.

*Rooting habit.*—Freely branching, moderately dense.

Plant description:

*Appearance/growth habit.*—Herbaceous decorative-type cut flower that is typically grown as a spray-type. Moderately vigorous growth habit.

*Flowering stem description.*—Aspect: Erect. Length: About 60 cm. Spray diameter: About 15 cm to 20 cm. Diameter: About 5 mm. Number of lateral branches: About seven to nine. Lateral branch length: About 15 cm to 20 cm. Lateral branch diameter: About 3 cm to 6 cm. Internode length: About 1 cm to 2 cm. Texture: Finely pubescent; longitudinally ridged. Color: Close to 146A to 146B.

*Foliage description.*—Arrangement: Alternate; simple. Length: About 6 cm to 10 cm. Width: About 5 cm to 7 cm. Apex: Cuspidate. Base: Attenuate. Margin: Palmately lobed; sinuses divergent. Texture, upper and lower surfaces: Pubescent, slightly rough; veins prominent on lower surface. Venation pattern: Pinnate, reticulate. Color: Developing foliage, upper surface: Close to 137C. Developing foliage, lower surface: Close to 146A. Fully expanded foliage, upper surface: Close to 147A; venation, close to 146A. Fully expanded foliage, lower surface: Between 146A and 147B; venation, 147B. Petiole: Length: About 2 mm to 3.5 cm. Diameter: About 2 mm to 3 mm. Texture, upper and lower surfaces: Slightly rough. Color, upper surface: Close to 146B. Color, lower surface: Close to 146C.

Inflorescence description:

*Appearance.*—Decorative-type inflorescence form with obovate-shaped ray florets. Inflorescences borne on terminals, arising from leaf axils. Ray and disc florets develop acropetally on a capitulum. Inflorescences slightly fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about seven weeks later when grown as a spray-type.

*Postproduction longevity.*—In an interior environment, inflorescences and foliage will maintain good color and substance for about four weeks. Inflorescences persistent.

*Quantity of inflorescences.*—Freely flowering habit; when grown as a spray type, about 25 inflorescences per flowering stem develop.

*Inflorescence size.*—Diameter: About 4.5 cm to 5 cm. Depth (height): About 1.5 cm. Disc diameter: About 1 cm to 1.5 cm. Receptacle height: About 2 mm. Receptacle diameter: About 2 mm to 3 mm. Receptacle color: Close to 145B to 145C.

*Inflorescence buds.*—Shape: Flattened spherical. Height: About 4 mm. Diameter: About 7 mm. Color: Between 144A and 137B.

*Ray florets.*—Length: About 1 cm to 2.2 cm. Width: About 6 mm to 9 mm. Shape: Obovate. Apex: Emarginate. Base: Attenuate. Margin: Entire. Angle: Initially upright to close to about 80° from vertical. Texture, upper and lower surfaces: Smooth, glabrous; satiny. Number per inflorescence: About 90 arranged in about nine whorls. Color: When opening, upper surface: Close to 69C; towards the apex, close to 77B. When opening, lower surface: Close to 69B; towards the apex, close to 77B. Fully opened, upper surface: Close to 76D. Fully opened, lower surface: Close to 76D; towards the apex, overlain with close to 75A.

*Disc florets.*—Shape: Fused tubular, elongated. Apex: Dentate. Length: About 4 mm to 5 mm. Diameter: About 0.5 mm to 1 mm. Number per inflorescence: About 15, massed at the center. Color: Apex: Close to 144A. Mid-section: Close to 153D. Base: Close to 145D.

*Involucral bracts.*—Length: About 5 mm. Width: About 3 mm. Shape: Ovate. Apex: Obtuse. Base: Obtuse to truncate. Margin: Entire. Texture, upper and lower surfaces: Smooth, glabrous. Number per inflorescence: About 20 arranged in two whorls. Color, upper surface: Close to 137C. Color, lower surface: Close to 137B.

*Peduncles.*—Length: About 9 cm to 13 cm. Diameter: About 1.5 mm to 2.5 mm. Angle: Erect to about 30° from vertical. Strength: Moderately strong. Texture: Pubescent; longitudinally ridged. Color: Close to 146B.

*Reproductive organs.*—Androecium: Not observed. Gynoecium: Present on both ray and disc florets. Style length: About 3 mm. Style color: Close to 145D. Stigma color: Close to 151A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Deknavona' as illustrated and described.

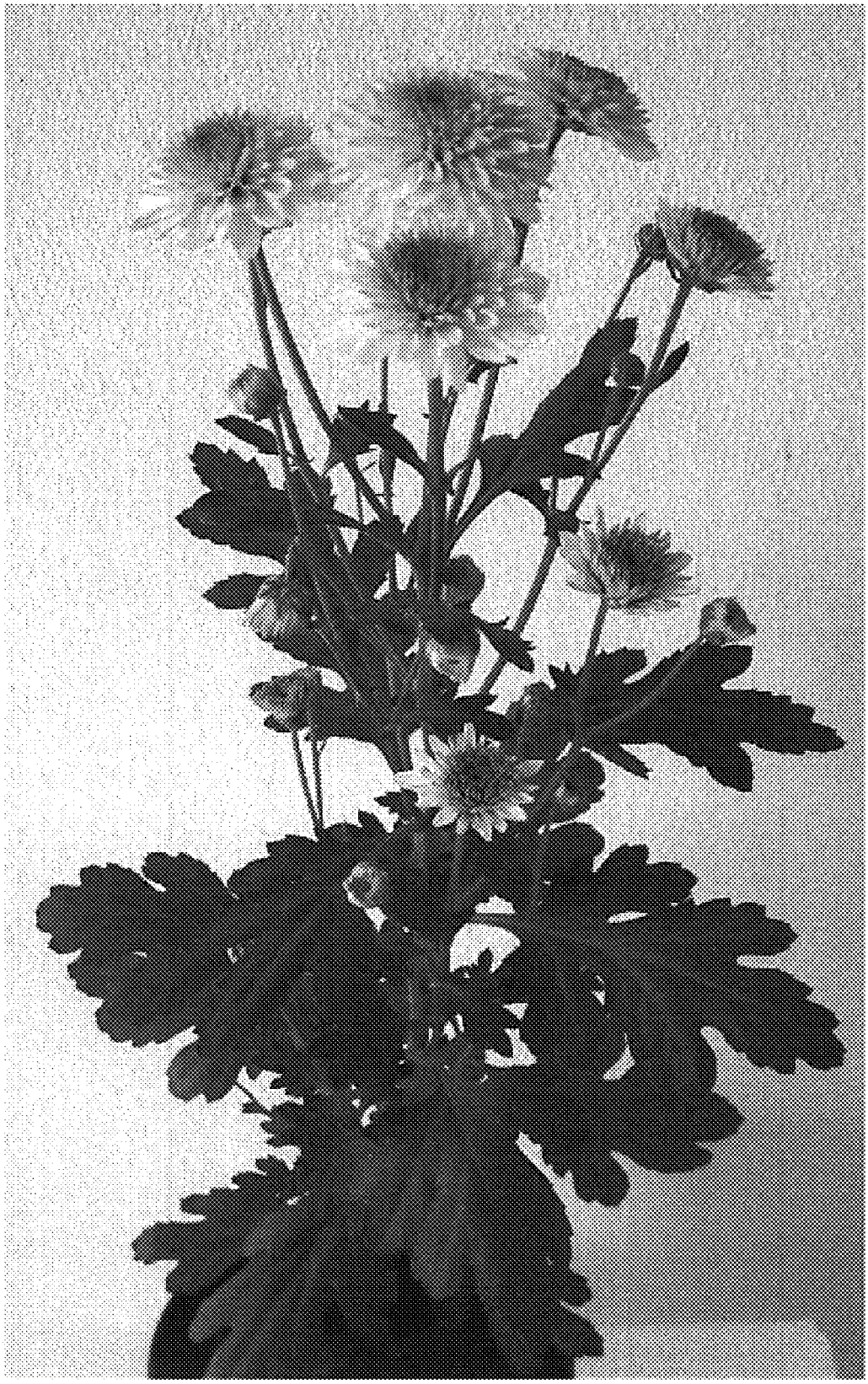

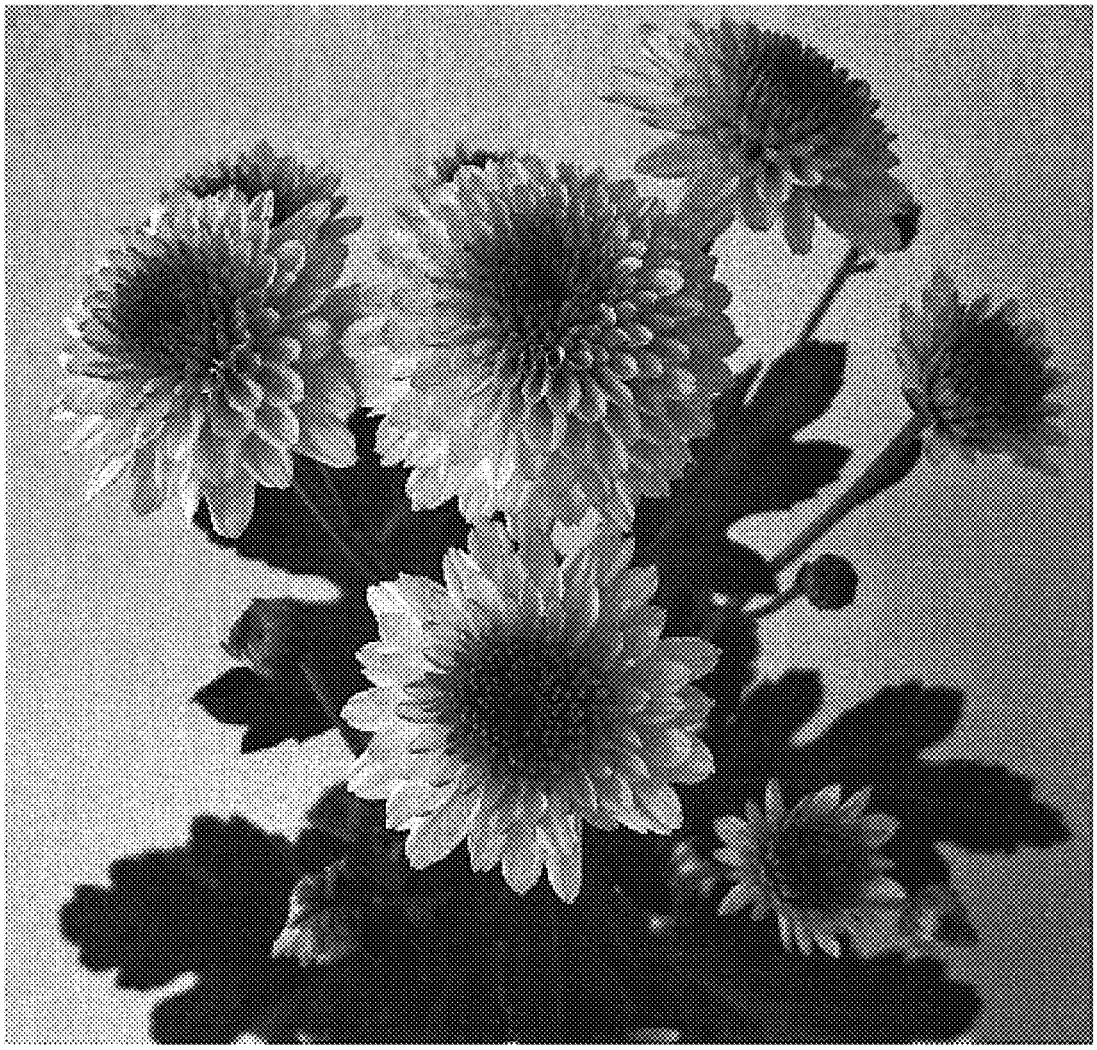

* * * * *